US00PP24608P3

(12) United States Plant Patent
Pressler

(10) Patent No.: US PP24,608 P3
(45) Date of Patent: Jul. 8, 2014

(54) LEMON TREE NAMED '7ELS1'

(50) Latin Name: *Citrus limon*
Varietal Denomination: 7ELS1

(75) Inventor: Craig Robert Pressler, Emerald (AU)

(73) Assignee: 2PH Farms Limited, Emerald, Queensland (AU)

( * ) Notice: Subject to any disclaimer, the term of this patent is extended or adjusted under 35 U.S.C. 154(b) by 100 days.

(21) Appl. No.: 13/507,221

(22) Filed: Jun. 12, 2012

(65) Prior Publication Data

US 2013/0333081 P1 Dec. 12, 2013

(51) Int. Cl.
*A01H 5/00* (2006.01)

(52) U.S. Cl.
USPC ..... Plt./201; Plt./156

(58) Field of Classification Search
USPC ..... Plt./201, 156
See application file for complete search history.

(56) References Cited

PUBLICATIONS

Official Journal of Plant Breeder's Rights Australia—Plant Varieties Journal, Quarter four: 2003,vol. 16, No. 4. (5 pages total).*

* cited by examiner

*Primary Examiner* — Susan McCormick Ewoldt
(74) *Attorney, Agent, or Firm* — Michelle Bos

(57) ABSTRACT

'7ELS1' is a new and distinct lemon tree notable for its high quality fruit with very few or no seeds.

1 Drawing Sheet

Genus and species: *Citrus limon.*
Variety denomination: '7ELS1'.

BACKGROUND AND SUMMARY OF THE VARIETY

The new lemon variety '7ELS1' originated as an induced mutation of 'Eureka' lemon (not patented). Varying degrees of Gamma irradiation from a Gammacell 200 (60C) source was applied to bud sticks of 'Eureka' in 1996 at St. Lucia, Queensland, Australia. The 1200 treated bud sticks were budded onto 'Carrizo' rootstock during June 1996, and the 1034 trees that survived were field planted at Emerald, Queensland, Australia during Autumn of 1997. As trees commenced fruiting, fruit from different branches on each tree were cut and inspected for seed numbers. This procedure was carried out during July of 1998, 1999 and 2000. The selection now known as '7ELS1' was identified as showing consistently lower seed numbers than the parent variety with no apparent reduction in fruit size. '7ELS1' also showed good fruit quality and good internal color in all three seasons. Budwood was taken from the original selection and budded to 'Benton' rootstock to establish mother trees. A further generation of trees was established by taking budwood from these mother trees and establishing granddaughter trees (again budded to 'Benton' rootstock), which were planted in 2003. All generations have consistently shown few or no seeds in each season.

'7ELS1' is a new and distinct lemon tree notable for its fruit, which produces consistently low numbers of seeds. Table 1 shows a comparison of '7ELS1' lemon to 'Eureka' and other similar (unpatented) varieties.

TABLE 1

Comparison of '7ELS1' to Known Varieties

| Plant Part | '7ELS1' | '7ELS3' | '3ELSO' |
|---|---|---|---|
| Tree: density of spines | Absent or sparse | Absent or sparse | Absent or sparse |
| Tree: length of spines | Very short | Very short | Short |
| Leaf blade: length | Medium | Medium | Medium |
| Leaf blade: shape in cross section | Straight or weakly concave | Straight or weakly concave | Straight or weakly concave |
| Leaf blade: twisting | Absent or weak | Absent or weak | Absent or weak |
| Leaf blade: undulation of margin | Absent or weak | Intermediate | Absent or weak |
| Leaf blade: emargination at tip | Absent | Absent | Absent |
| Style: length | Short to medium | Medium to long | Medium |
| Fruit: ratio length/diameter | Medium | Large | Medium |
| Fruit: position of broadest part | At middle | At middle | At middle |
| Fruit: general shape of proximal part | Strongly rounded | Strongly rounded | Slightly rounded |
| Fruit rind: thickness | Thin to medium | Thin | Thin to medium |
| Fruit: number of seeds | Absent or very few | Few to medium | Varies, absent or very few to few |

TABLE 1-continued

| Plant Part | 'Code 3X97' | 'Code 7B97' | 'Eureka' |
|---|---|---|---|
| Tree: density of spines | Intermediate | Absent or sparse | Absent or sparse |
| Tree: length of spines | Short | Very short | Short |
| Leaf blade: length | Medium | Medium | Medium to long |
| Leaf blade: shape in cross section | Intermediate | Straight or weakly concave | Straight or weakly concave |
| Leaf blade: twisting | Intermediate | Absent or weak | Absent or weak |
| Leaf blade: undulation of margin | Absent or weak | Absent or weak | Absent or weak |
| Leaf blade: emargination at tip | Present | Absent | Absent |
| Style: length | Short to medium | Medium | Medium |
| Fruit: ratio length/diameter | Medium | Medium | Medium |
| Fruit: position of broadest part | Towards distal end | At middle | At middle |
| Fruit: general shape of proximal part | Strongly rounded | Strongly rounded | Strongly rounded |
| Fruit rind: thickness | Thin to medium | Thin to medium | Medium |
| Fruit: number of seeds | Absent or very few | Varies, absent or very few to few | Many |

BRIEF DESCRIPTION OF THE PHOTOGRAPHS

FIG. 1 shows whole and sectioned fruit of '7ELS1' lemon.

Because lighting conditions can affect the colors shown in photographic illustrations, color characteristics of this new variety should be determined with reference to the observations described herein, rather than from the illustrations alone.

DETAILED BOTANICAL DESCRIPTION

The following detailed botanical description is based on observations of trees and fruit of '7ELS1', budded to 'Benton' rootstock (not patented) and planted in 2003. Observations were recorded and photographs taken during the 2006 and 2011 growing seasons at Munduberra, Queensland, Australia. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average. Colors are described with reference to The Royal Horticultural Society Colour Chart ($5^{th}$ Ed., 2007).

Tree:

*Vigor.*—Vigorous.
*Density of canopy.*—Dense.
*Height.*—3 m.
*Spread.*—3 m.
*Trunk diameter* (*at* 30 *cm above graft*).—140 mm.
*Bark texture.*—Smooth.
*Bark color.*—Brown 163D, N187A.
*Lenticel size.*—1 mm.
*Lenticel color.*—Brown N187A.
*Lenticel quantity.*—Many.
*Tendency toward alternate bearing.*—None.
*Winter hardiness.*—Not tolerant to cold; prolonged temperatures below zero will damage shoots and fruit (same as 'Eureka').
*Chilling requirement.*—None (same as 'Eureka').
*Drought tolerance.*—Somewhat tolerant (same as 'Eureka').

Branch (fruiting branch located about 1 m above graft union):

*Length.*—80 cm.
*Diameter.*—60 mm.
*Crotch angle.*—30°.
*Bark color.*—Greyed-orange 163D; brown N187A.
*Bark texture.*—Smooth.
*Density of spines.*—Absent or sparse.
*Length of spines.*—Very short, 5 mm.
*Color of current year shoot.*—Green 140A.

Young leaf:

*Presence of anthocyanin coloration.*—Present.
*Intensity of anthocyanin coloration.*—Weak.

Leaf blade:

*Length.*—Medium, 104 mm.
*Width.*—Medium, 56 mm.
*Ratio length/width.*—Medium, 1.85.
*Shape in cross section.*—Straight or weakly concave.
*Leaf arrangement.*—Alternate.
*Leaf shape.*—Elliptic.
*Leaf veins.*—Pinnate arrangement, green 143A, 143B.
*Apex shape.*—Acute.
*Base shape.*—Cuneate.
*Emargination at tip.*—Absent.
*Twisting.*—Absent or weak.
*Color of upper surface.*—Green 143B.
*Color of lower surface.*—Green 145.
*Undulation of margin.*—Absent or weak.
*Incisions of margin.*—Crenate.
*Texture.*—Smooth.

Petiole:

*Length.*—12 mm.
*Diameter.*—3 mm.
*Color.*—Green N144D.
*Presence of wings.*—Absent.

Flower bud:

*Bud shape.*—Oval.
*Bud length.*—2.2 mm.
*Bud diameter.*—1 mm.
*Bud color.*—Green 144.
*Presence of anthocyanin coloration.*—Present.
*Intensity of anthocyanin coloration.*—Medium.

Flower:

*Quantity of flowers per cluster.*—4 to 7.
*Blossom diameter.*—23 mm.
*Blossom depth.*—18 mm.
*Pollen present.*—No.
*Pollinator.*—None required — '7ELS1' is parthenocarpic.
*Sepal length.*—4.5 mm.
*Sepal width.*—4.5 mm.
*Sepal color—upper surface.*—Yellow 2B.
*Sepal color—lower surface.*—Yellow 3B.
*Quantity of petals per flower.*—5.
*Petal shape.*—Elongated arch.
*Petal margin.*—Smooth.
*Petal length.*—17 mm.

*Petal width.*—5.1 mm.
*Petal color—upper surface.*—Cream NN155D.
*Petal color—lower surface.*—Cream NN155D, purple 84D.
*Pedicel length.*—4.75 mm.
*Pedicel diameter.*—1.8 mm.
*Pedicel color.*—Green 151C.
*Pistil quantity per flower.*—1.
*Pistil length.*—12.4 mm.
*Length of stamens.*—Medium.
*Basal union of stamens.*—Present.
*Anther quantity per flower.*—1.
*Anther length.*—2.7 mm.
*Stigma quantity per flower.*—1.
*Stigma length.*—2 mm.
*Style quantity per flower.*—1.
*Style length.*—6.4 mm.
*Style color.*—Yellow 1B.
*Ovary quantity per flower.*—1.
*Ovary length.*—4.7 mm.
*Ovary diameter.*—2.7 mm.
*Ovary color.*—Green 144A.
*Diameter of calyx.*—Medium, about 6.8 mm to 7.3 mm.
*Fragrance.*—Sweet with a background cinnamon note.
*Date of first bloom.*—Late August.
*Date of full bloom.*—Early September.
*Date of first fruitlet fall.*—November.

Fruit:
*Clustering of fruits.*—Present.
*Axial diameter.*—80 mm.
*Apical diameter.*—60 mm.
*Weight.*—160 g.
*Position of broadest part.*—At middle.
*General shape in profile.*—Oval.
*General shape of proximal part.*—Strongly rounded.
*Presence of neck.*—Present.
*Length of neck* (*necked varieties only*).—Very short, 0 to about 8 mm.
*General shape of distal part.*—Slightly rounded.
*Presence of nipple.*—Present.
*Prominence of nipple.*—Weak to medium.
*Presence of radial grooves at distal end.*—Present.
*Expression of radial grooves at distal end.*—Very weak.
*Colour of variegation.*—Absent.

Fruit surface:
*Color.*—Green 140B.
*Glossiness.*—Weak.
*Rind texture.*—Smooth.
*Size of oil glands.*—1 mm.
*Quantity of oil glands.*—40 per $cm^2$.

Fruit rind:
*Thickness.*—Thin to medium, 4.3 mm.
*Ease of peeling.*—Difficult.
*Albedo thickness.*—4 mm.
*Albedo color.*—Yellow 2C.

Fruit flesh:
*Main colour of flesh.*—Yellow 2C.
*Quantity of segments per fruit.*—8.
*Presence of rudimentary segments.*—Absent or weak.
*Toughness of segment membrane.*—Moderate.
*Juice sac length.*—8 mm.
*Juice sac shape.*—Elongated.
*Juice sac length to width ratio.*—8:1.5.
*Juice sac color.*—Yellow 2C.
*Juice soluble solids* (° *Brix*).—7.3.

Seeds (open pollination):
*Number of seeds.*—Absent or very few.

Stem:
*Length.*—2 cm.
*Diameter.*—4 mm.
*Color.*—Green 144.

Harvest:
*Relative harvest maturity.*—Early.
*Harvest window.*—January-December (in region tested).

Yield: 50 to 100 tons per hectare.
Market use: Fresh.
Shipping characteristics: Similar to other known lemon varieties.
Storage characteristics: Sensitive to storage below −1 degree C.

The invention claimed is:

1. A new and distinct variety of lemon tree, substantially as illustrated and described herein.

* * * * *

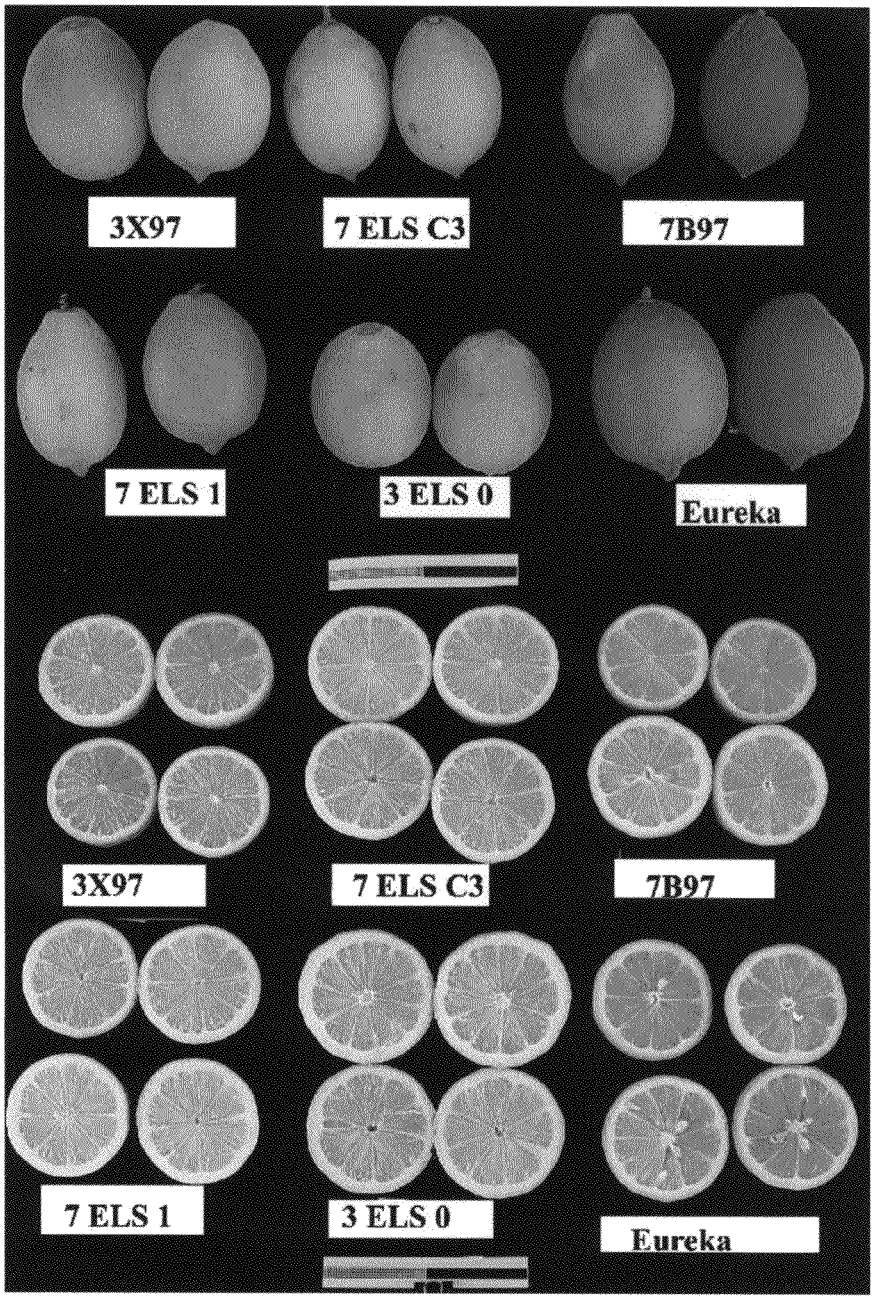
3X97
7 ELS C3
7B97
7 ELS 1
3 ELS 0
Eureka
3X97
7 ELS C3
7B97
7 ELS 1
3 ELS 0
Eureka